(12) United States Patent
Kitahara et al.

(10) Patent No.: US 11,580,199 B2
(45) Date of Patent: Feb. 14, 2023

(54) CORRESPONDENCE OF EXTERNAL OPERATIONS TO CONTAINERS AND MUTATION EVENTS

(71) Applicant: INTERNATIONAL BUSINESS MACHINES CORPORATION, Armonk, NY (US)

(72) Inventors: Hirokuni Kitahara, Tokyo (JP); Yuji Watanabe, Tokyo (JP); Fumiko Akiyama, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 670 days.

(21) Appl. No.: 16/577,108

(22) Filed: Sep. 20, 2019

(65) Prior Publication Data

US 2021/0089631 A1 Mar. 25, 2021

(51) Int. Cl.
 *H04N 7/16* (2011.01)
 *G06F 7/04* (2006.01)
 (Continued)

(52) U.S. Cl.
 CPC .......... *G06F 21/121* (2013.01); *G06F 9/3891* (2013.01); *G06F 16/182* (2019.01); *G06F 16/90335* (2019.01)

(58) Field of Classification Search
 CPC . G06F 21/121; G06F 16/182; G06F 16/90335
 (Continued)

(56) References Cited

U.S. PATENT DOCUMENTS

| 9,740,460 B2 * | 8/2017 | Duffy | G06F 8/437 |
| 2014/0196008 A1 * | 7/2014 | Duffy | G06F 8/315 |
| | | | 717/116 |

(Continued)

FOREIGN PATENT DOCUMENTS

| CN | 1529248 A | 9/2004 |
| CN | 103226675 A | 7/2013 |

(Continued)

OTHER PUBLICATIONS

Jack S. Hale; Containers for Portable, Productive, and Performant Scientific Computing; IEEE:2017; pp. 40-50.*

(Continued)

*Primary Examiner* — Monjur Rahim
(74) *Attorney, Agent, or Firm* — Tutunjian & Bitetto, P.C.; Randy Emilio Tejeda

(57) ABSTRACT

A method is provided for determining command-to-process correspondence. The method includes identifying, by the hardware processor, initial processes resulting from executions of container immutability change events for each of multiple containers in a cluster, based on an execution time, a process identifier and a process group identifier for each of the container immutability change events. The method further includes checking, by the hardware processor, if an initial process from among the identified initial processes matches an entry in a database that stores external container commands and at least one respective process resulting from executing each of the external container commands. The method also includes designating, by the hardware processor, a particular external command, from among the external container commands stored in the database, as having a correspondence to the initial process, responsive to the initial process matching the at least one respective process resulting from executing the particular external command.

25 Claims, 9 Drawing Sheets

(51) Int. Cl.
   *G06F 21/12* (2013.01)
   *G06F 16/182* (2019.01)
   *G06F 16/903* (2019.01)
   *G06F 9/38* (2018.01)

(58) Field of Classification Search
   USPC .......................................................... 726/26
   See application file for complete search history.

(56) References Cited

U.S. PATENT DOCUMENTS

| | | | | |
|---|---|---|---|---|
| 2014/0283031 A1* | 9/2014 | Eksten | ................. | G06F 21/105 |
| | | | | 726/22 |
| 2018/0157825 A1* | 6/2018 | Eksten | .................... | G06F 21/51 |
| 2018/0293374 A1* | 10/2018 | Chen | .................... | G06F 9/45558 |
| 2018/0329693 A1* | 11/2018 | Eksten | ..................... | G06F 8/65 |
| 2019/0190776 A1* | 6/2019 | Bregman | .............. | G06F 9/5072 |
| 2019/0370225 A1* | 12/2019 | Saradhi | ................. | G06F 16/185 |
| 2021/0326435 A1* | 10/2021 | Klonowski | ........... | G06F 21/554 |
| 2021/0326438 A1* | 10/2021 | Dichiu | ................. | G06F 3/0604 |

FOREIGN PATENT DOCUMENTS

| | | |
|---|---|---|
| CN | 106790291 A | 5/2017 |
| CN | 110046505 A | 7/2019 |
| WO | WO 2018/224243 A1 | 12/2018 |

OTHER PUBLICATIONS

International Search Report dated Nov. 30, 2020 for International Application No. PCT/IB2020/057672.

Zhu et al., "Avoiding the Disk Bottleneck in the Data Domain Deduplication File System", FAST '08: 6th USENIX Conference on File and Storage Technologies, Dec. 2008, pp. 269-282.

Mell et al. "The NIST Definition of Cloud Computing", NIST Special Publication 800-145, 2011, 7 pages.

* cited by examiner

```
$ kubectl cp -n mutation-advisor sample_data_collection.sh python-test-1:./
$ kubectl exec -it -n mutation-advisor python-test-1 sh sample_data_collection.sh
$ kubectl exec -it -n mutation-advisor python-test-1 -- ls -l
```

CORRESPONDENCE OF EXTERNAL OPERATIONS TO CONTAINERS AND MUTATION EVENTS

BACKGROUND

The present invention generally relates to information processing, and more particularly to correspondence of external operations to containers and mutation events. A container can be a minimum package of a cloud application, which runs using a pre-built image. Currently, container immutability, which refers to not changing a container since its build time, is an important policy in cloud and other applications. However, users can change files and execute processing in a running container from outside of the container, using an external operation. File change events and/or process execution events that are generated by this kind of (external) operation are referred to as "mutation events". A single external operation can generate a large number of mutation events, so it is difficult to find correspondence by checking them manually. Thus, there is a need for an automated, computer-based approach to determine the correspondence between external operations and mutation events.

SUMMARY

According to an aspect of the present invention, a computer-implemented method is provided for determining command-to-process correspondence. The method includes identifying, by the hardware processor, initial processes resulting from executions of container immutability change events for each of multiple containers in a cluster, based on an execution time, a process identifier and a process group identifier for each of the container immutability change events. The method further includes checking, by the hardware processor, if an initial process from among the identified initial processes matches an entry in a database that stores external container commands and at least one respective process resulting from executing each of the external container commands. The method also includes designating, by the hardware processor, a particular external command, from among the external container commands stored in the database, as having a correspondence to the initial process, responsive to the initial process matching the at least one respective process resulting from executing the particular external command.

According to another aspect of the present invention, a computer program product is provided for determining command-to-process correspondence. The computer program product includes a non-transitory computer readable storage medium having program instructions embodied therewith. The program instructions are executable by a computer to cause the computer to perform a method. The method includes identifying, by the hardware processor, initial processes resulting from executions of container immutability change events for each of multiple containers in a cluster, based on an execution time, a process identifier and a process group identifier for each of the container immutability change events. The method further includes checking, by the hardware processor, if an initial process from among the identified initial processes matches an entry in a database that stores external container commands and at least one respective process resulting from executing each of the external container commands. The method also includes designating, by the hardware processor, a particular external command, from among the external container commands stored in the database, as having a correspondence to the initial process, responsive to the initial process matching the at least one respective process resulting from executing the particular external command.

According to yet another aspect of the present invention, a computer processing system is provided for determining command-to-process correspondence. The computer processing system includes a memory device including program code stored thereon. The computer processing system further includes a hardware processor, operatively coupled to the memory device, and configured to run the program code stored on the memory device to identify initial processes resulting from executions of container immutability change events for each of multiple containers in a cluster, based on an execution time, a process identifier and a process group identifier for each of the container immutability change events. The hardware processor further runs the program code to check if an initial process from among the identified initial processes matches an entry in a database that stores external container commands and at least one respective process resulting from executing each of the external container commands. The hardware processor also runs the program code to designate a particular external command, from among the external container commands stored in the database, as having a correspondence to the initial process, responsive to the initial process matching the at least one respective process resulting from executing the particular external command.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 7 is a block diagram showing yet another exemplary table, in accordance with an embodiment of the present invention;

DETAILED DESCRIPTION

Embodiments of the present invention are directed to correspondence of external operations to containers and mutation events.

One or more embodiments of the present invention enable a user to identify the correspondence between external operations to containers and mutation events. In this way, mutable containers can be transformed into immutable containers based on the identified correspondence and deployed in a computing environment. In an embodiment, the computing environment can be a cloud computing environment.

One or more embodiments of the present invention utilize a process structure analysis (see, e.g., FIGS. 2-3) in order to identify the correspondence between external operations to container and mutation events. In an embodiment, the process structure analysis involves identifying initial processes that are mutated by a given external operation based on, e.g., execution time, process ID ad process group ID, for each change event considered by the present invention.

While one or more embodiments of the present invention are described with respect to Kubernetes® commands for the sake of illustration, other external commands can also be used, while maintaining the spirit of the present invention.

Thus, the present invention enables the identification of correspondence between an external operation and a resulting mutation event with respect to a mutable container, and can further enable the transformation of the mutable container so identified into an immutable container by "breaking" or otherwise eliminating the correspondence and/or using other techniques. An immutable object is inherently safer than a mutable object, as well as possessing other benefits over a mutable object.

Figure 1:
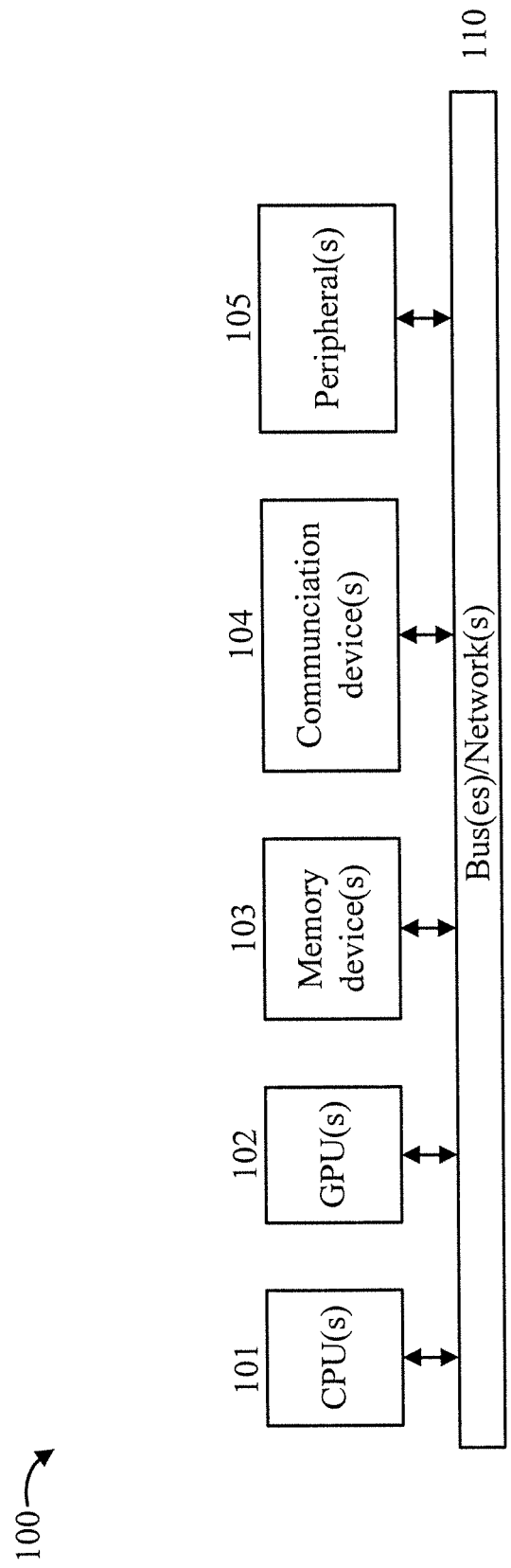
FIG. 1 is a block diagram showing an exemplary processing system, in accordance with an embodiment of the present invention.

FIG. 1 is a block diagram showing an exemplary processing system 100, in accordance with an embodiment of the present invention. The processing system 100 includes a set of processing units (e.g., CPUs) 101, a set of GPUs 102, a set of memory devices 103, a set of communication devices 104, and set of peripherals 105. The CPUs 101 can be single or multi-core CPUs. The GPUs 102 can be single or multi-core GPUs. The one or more memory devices 103 can include caches, RAMs, ROMs, and other memories (flash, optical, magnetic, etc.). The communication devices 104 can include wireless and/or wired communication devices (e.g., network (e.g., WIFI, etc.) adapters, etc.). The peripherals 105 can include a display device, a user input device, a printer, an imaging device, and so forth. Elements of processing system 100 are connected by one or more buses or networks (collectively denoted by the figure reference numeral 110).

In an embodiment, memory devices 103 can store specially programmed software modules to transform the computer processing system into a special purpose computer configured to implement various aspects of the present invention. In an embodiment, special purpose hardware (e.g., Application Specific Integrated Circuits, Field Programmable Gate Arrays (FPGAs), and so forth) can be used to implement various aspects of the present invention.

In an embodiment, memory devices 103 can implement a database storing external container commands and at least one respective process resulting from executing each of the external container commands. In an embodiment, the at least one respective process can be an index to the corresponding external container command. In such a case, the memory devices can include a content addressable or associative memory. In an embodiment, memory devices 103 can implement a database storing mutable containers. In an embodiment, memory devices 103 can implement a database storing immutable containers transformed from mutable containers.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. Further, in another embodiment, a cloud configuration can be used (e.g., see FIGS. 8-9). These and other variations of the processing system 100 are readily contemplated by one of ordinary skill in the art given the teachings of the present invention provided herein.

Moreover, it is to be appreciated that various figures as described below with respect to various elements and steps relating to the present invention that may be implemented, in whole or in part, by one or more of the elements of system 100.

As used herein, the term "hardware processor subsystem" or "hardware processor" in short refers to a processor, memory, and software combination that cooperate to perform one or more specific tasks. In an embodiment, the hardware processor subsystem can include one or more data processing elements (e.g., logic circuits, etc.). In an embodiment, the one or more data processing elements can be included in a central processing unit, a graphics processing unit, and/or a separate processor or computing element-based (e.g., logic gates, etc.) controller. In an embodiment, the hardware processor subsystem can include one or more on-board memories (e.g., caches). In an embodiment, the hardware processor subsystem can include one or more other memories (e.g., ROM, RAM, BIOS). In an embodiment, the hardware processor subsystem can include and execute one or more software applications. In an embodiment, the one or more software applications can include the operating system and/or one or more other applications and/or specific code to achieve a specified result. These and other variations of a hardware processor subsystem are readily determined given the teachings of the present invention provided herein.

Figure 2:
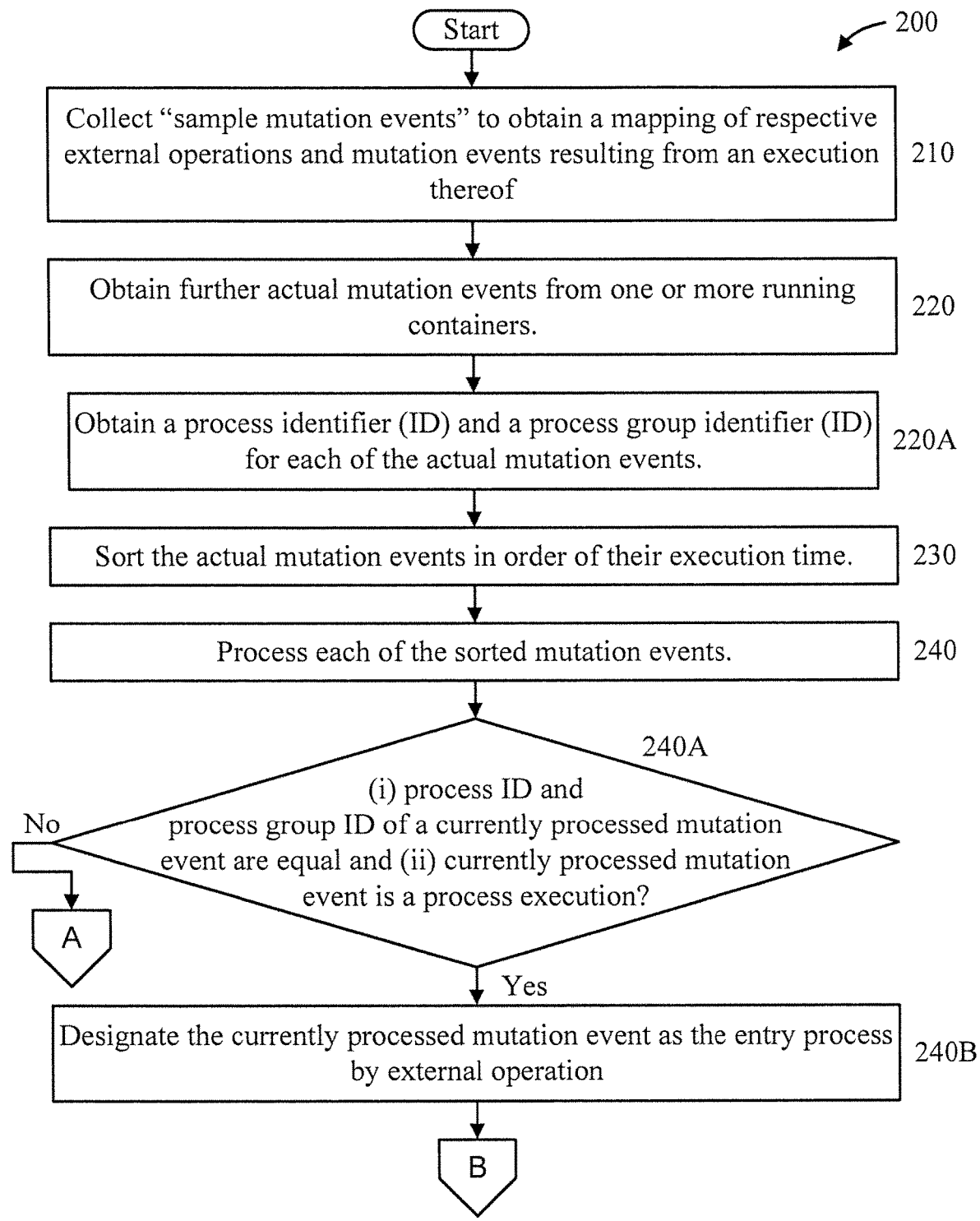
FIGS. 2-3 are flow diagrams showing an exemplary method for determining correspondence of external operations to containers and mutation, in accordance with an embodiment of the present invention.
Figure 3:
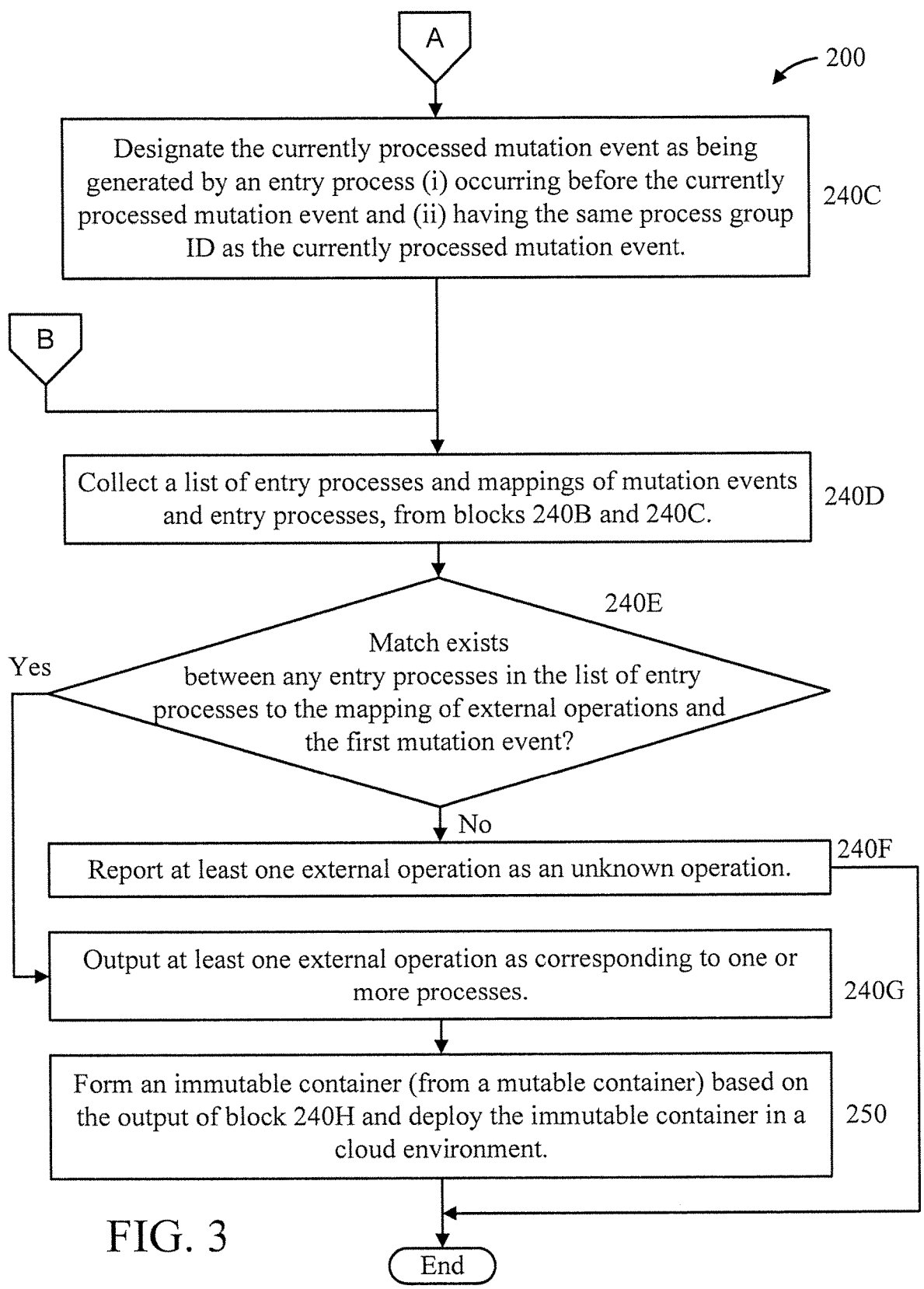

FIGS. 2-3 are flow diagrams showing an exemplary method 200 for determining correspondence of external operations to containers and mutation, in accordance with an embodiment of the present invention.

At block 210, collect "sample mutation events" to obtain a mapping of respective external operations and mutation events resulting from an execution thereof. The external operations can be obtained from a set of external operations. For a given external operation, one or more mutation events to be mapped thereto can be obtained from a set of mutation events that result from an execution of the given external operation. A set of these events can be used as training data, so this data is prepared first. As used herein, the terms "sample mutation event" and "mutation event" in short refer to a sample observed mutation event resulting from executing a corresponding external operation. The sample mutation events that result from executing a respective external operation are observed by a certain existing method, such as "system call tracing".

For example, in an embodiment, block 210 can involve executing an external command (e.g., a kubectl exec command, which executes a command against a container in a pod), obtaining corresponding mutation events resulting from the execution of the external commend, and creating a mapping of the (kubectl exec) external command and the first mutation event (from among the corresponding mutation events). While a kubectl command is used for the sake of illustration, other (container) external commands can also be used to cause mutation events to be generated.

At block 220, obtain further actual mutation events from one or more running containers. A running container is one that is executing one or more processes/commands. It is to be noted that the mutation events of block 210 are also actual mutation events from a prior actual execution.

In an embodiment, the mutation events can be obtained in any of blocks 210 and 220 by one or more techniques such as system call tracing and system scanning. In system call tracing, an Operating system (OS) generates a lot of system calls during its operation, and every container uses the OS for its tasks. When some external operations are executed by a container, OS software in the container will generate a set of system calls. A part of those system calls are the mutation events.

As another example, in system scanning, a container will be scanned periodically, and the system will save a summary of scanned files and processes. When there are some differences among scans, the container has a file/process which has been mutated.

In an embodiment, block 220 can include block 220A.

At block 220A, obtain a process identifier (ID) and a process group identifier (ID) for each of the actual mutation events.

At block 230, sort the actual mutation events in order of their execution time.

At block 240, process each of the sorted mutation events.

In an embodiment, block 240 can include one or more of blocks 240A through 240I.

At block 240A, determine whether (i) the process ID and the group process ID of currently processed mutation event are equal and (ii) the currently processed mutation event is a process execution. If so (for both (i) and (ii)), then proceed to block 240B. Otherwise (if one or both are not true), proceed to block 240C.

At block 240B, designate the currently processed mutation event as the entry process by external operation (or "entry process" in short).

At block 240C, designate the currently processed mutation event as being generated by an entry process (i) occurring before the currently processed mutation event and (ii) having the same process group ID as the currently processed mutation event.

At block 240D, collect a list of entry processes and mappings of mutation events and entry processes, from blocks 240B and 240C.

At block 240E, determine if a match exists between any of the entry processes in the list of entry processes (collected by block 240D) to the mapping of external operations and the first mutation event (prepared by block 210). If so, then proceed to block 240G. Otherwise, proceed to block 240F.

At block 240F, output at least one external operation as corresponding to one or more processes. In an embodiment relating to a kubectl operation, the output can be in the form as follows: kubectl [command] [TYPE] [NAME]-o<output_format>.

At block 240G, report at least one external operation as an unknown operation. Moreover, in an embodiment, block 240G can further involve triggering some additional learning (preparation) to improve the mapping obtained at block 210.

At block 250, form an immutable container (from a mutable container) based on the output of block 240H (namely the correspondence between the at least one external operation and the one or more corresponding processes) and deploy the immutable container in a cloud environment. Thus, block 250 can transform one or more mutable containers into immutable containers at least with respect to the mutation events that previously caused mutation. In an embodiment, the container is reformulated (rewritten) to be immutable when encountering the at least one external operation. For example, the container code can be rewritten or some code removed so the remaining container code is no longer responsive to (affected by) the external operations and is thus immutable with respect to the external commands. Also, this system can be used for identifying/removing the root cause of the mutation, because finding the operator of some external operations is usually easy. The external operations will be logged into the corresponding API server, for example, the "kubectl exec" command is logged in the Kubernetes® API server log. So, once mutations are detected and external operation is identified, the system can also find/report a person who makes the mutation.

Figure 4:
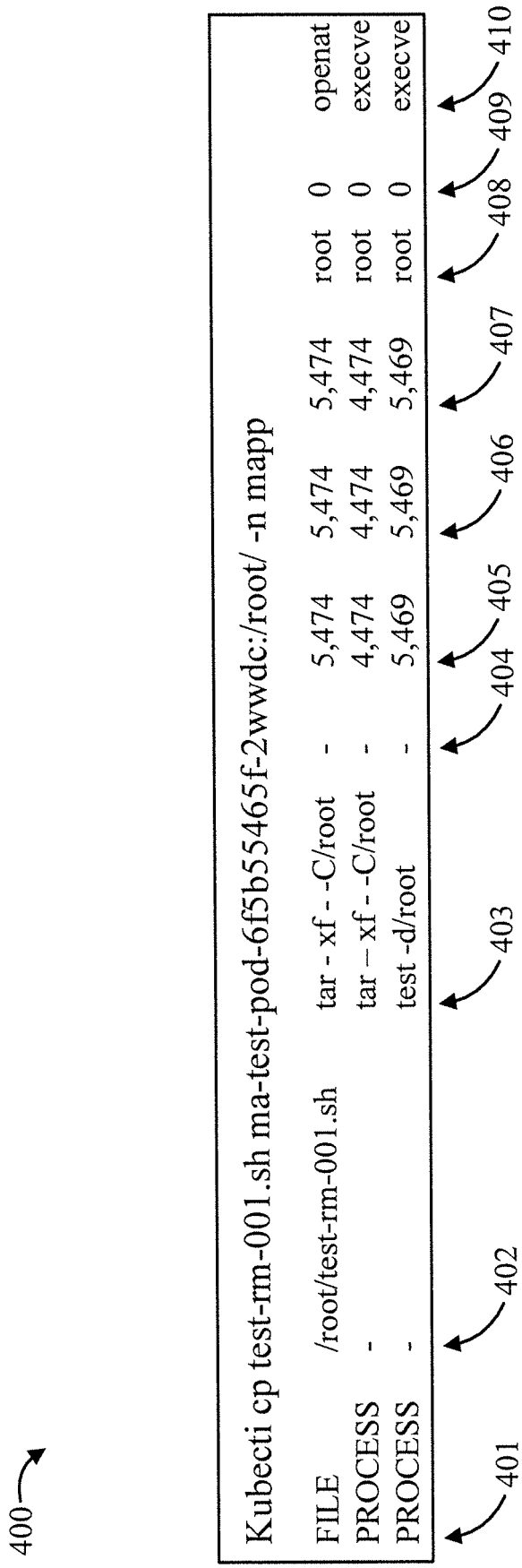
FIG. 4 is a block diagram showing an exemplary mapping of external operations and the first mutation event, in accordance with an embodiment of the present invention.

FIG. 4 is a block diagram showing an exemplary mapping 400 of external operations and the first mutation event, in accordance with an embodiment of the present invention. Mapping 400 corresponds to an embodiment of block 210 of FIG. 2.

Figure 5:
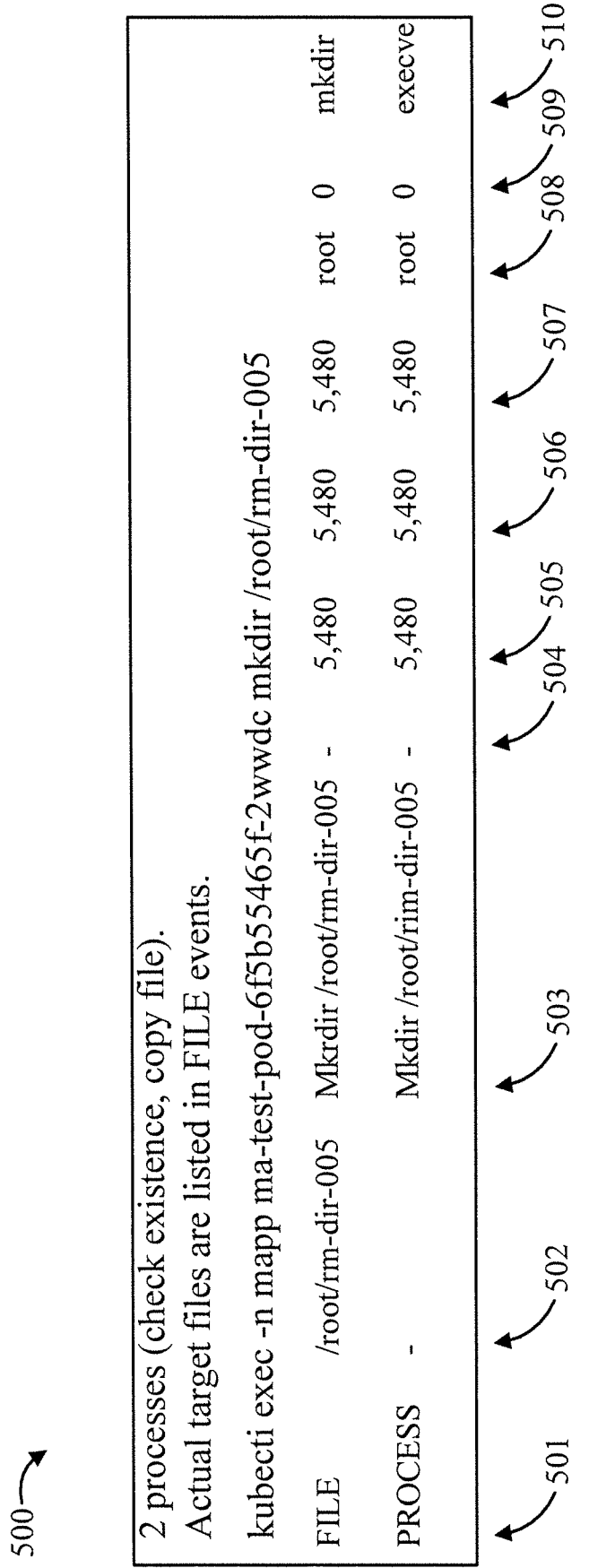
FIG. 5 is a block diagram showing an exemplary table, in accordance with an embodiment of the present invention.

In FIG. 4, the column designations for columns 401 through 410 of the mapping 400 are as follows:
  401: mutation type
  402: filename
  403: process command
  404: (unused column)
  405: process ID
  406: process group ID
  407: process session ID
  408: user name
  409: user ID
  410: system call type FIG. 5 is a block diagram showing an exemplary table 500, in accordance with an embodiment of the present invention. Table 500 corresponds to an embodiment of block 240C of FIG. 2.

Figure 6:
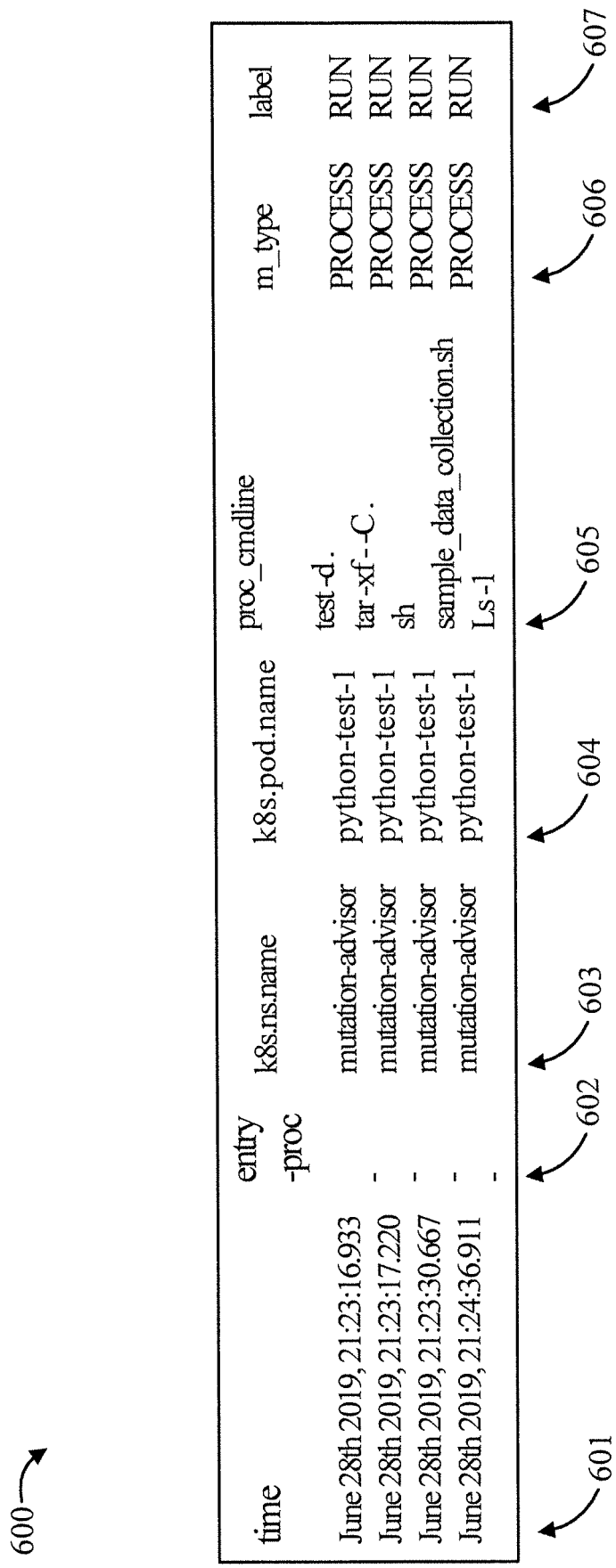
FIG. 6 is a block diagram showing another exemplary table, in accordance with an embodiment of the present invention.

In FIG. 5, the column designations for columns 501 through 510 of the table 500 are as follows:
  501: mutation type
  502: filename
  503: process command
  504: (unused column)
  505: process ID
  506: process group ID
  507: process session ID
  508: user name
  509: user ID
  510: system call type FIG. 6 is a block diagram showing an exemplary table 600, in accordance with an embodiment of the present invention. Table 600 corresponds to an embodiment of block 240B of FIG. 2.

In FIG. 6, the column designations for columns 601 through 607 of the table 600 are as follows
  601: execution time
  602: entry process (unused column)
  603: Kubernetes® namespace name
  604: Kubernetes® pod name
  605: process command 606: mutation type 607: mutation operation type The table includes 4 entry processes, namely: (1) test-d; (2) tar-xf--C; (3) sh sample_data_collection.sh; and (4) ls-1; and. The 4 entry processes result from 3 external operations in FIG. 7.

FIG. 7 is a block diagram showing an exemplary table 700, in accordance with an embodiment of the present invention. Table 700 corresponds to an embodiment of block 240G of FIG. 2.

The table 700 includes 3 kubectl commands, namely: (1) kubectl cp-n mutation-advisor sample_data_collection.sh python-test-1:./; (2) kubectl exec-it-n mutation-advisor python-test-1 sh sample_data_collection.sh; and (3) kubectl exec-it-n mutation-advisor python-test-1-ls-1.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
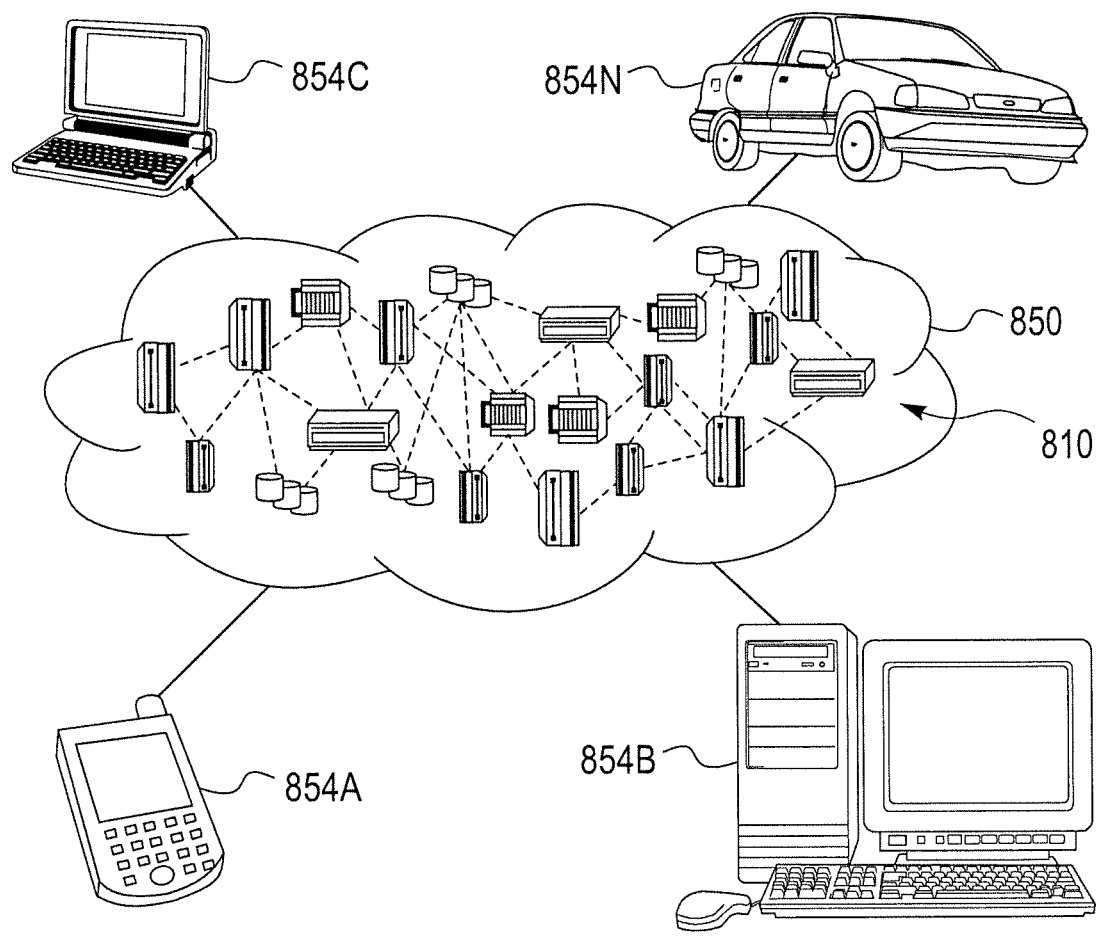
FIG. 8 is a block diagram showing an illustrative cloud computing environment having one or more cloud computing nodes with which local computing devices used by cloud consumers communicate, in accordance with an embodiment of the present invention.

Referring now to FIG. 8, illustrative cloud computing environment 850 is depicted. As shown, cloud computing environment 850 includes one or more cloud computing nodes 810 with which local computing devices used by cloud consumers, such as, for example, personal digital assistant (PDA) or cellular telephone 854A, desktop computer 854B, laptop computer 854C, and/or automobile computer system 854N may communicate. Nodes 810 may communicate with one another. They may be grouped (not shown) physically or virtually, in one or more networks, such as Private, Community, Public, or Hybrid clouds as described hereinabove, or a combination thereof. This allows cloud computing environment 850 to offer infrastructure, platforms and/or software as services for which a cloud consumer does not need to maintain resources on a local computing device. It is understood that the types of computing devices 854A-N shown in FIG. 8 are intended to be illustrative only and that computing nodes 810 and cloud computing environment 850 can communicate with any type of computerized device over any type of network and/or network addressable connection (e.g., using a web browser).

Figure 9:
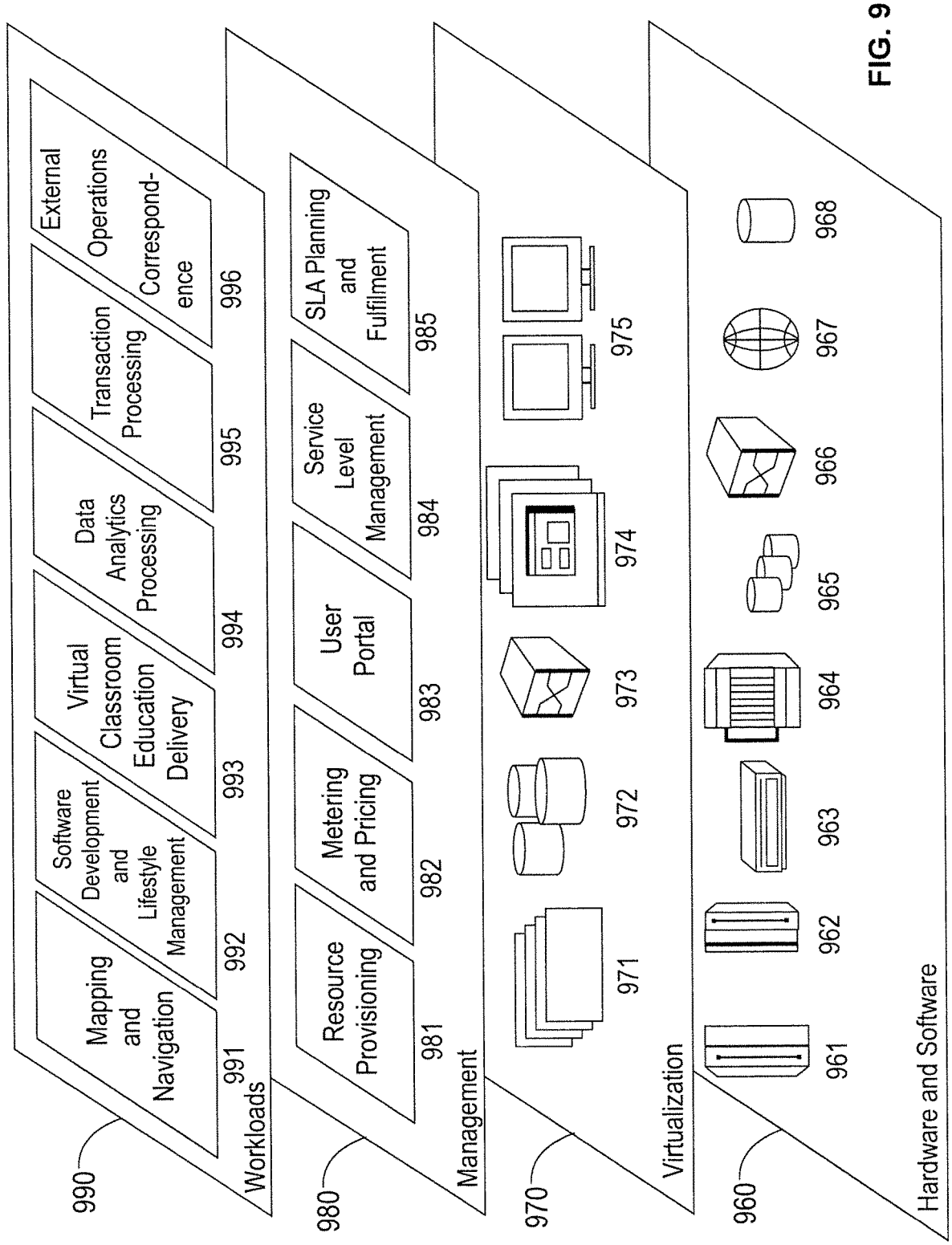
FIG. 9 is a block diagram showing a set of functional abstraction layers provided by a cloud computing environment, in accordance with an embodiment of the present invention.

Referring now to FIG. 9, a set of functional abstraction layers provided by cloud computing environment 850 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 960 includes hardware and software components. Examples of hardware components include: mainframes 961; RISC (Reduced Instruction Set Computer) architecture based servers 962; servers 963; blade servers 964; storage devices 965; and networks and networking components 966. In some embodiments, software components include network application server software 967 and database software 968.

Virtualization layer 970 provides an abstraction layer from which the following examples of virtual entities may be provided: virtual servers 971; virtual storage 972; virtual networks 973, including virtual private networks; virtual applications and operating systems 974; and virtual clients 975.

In one example, management layer 980 may provide the functions described below. Resource provisioning 981 provides dynamic procurement of computing resources and other resources that are utilized to perform tasks within the cloud computing environment. Metering and Pricing 982 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 983 provides access to the cloud computing environment for consumers and system administrators. Service level management 984 provides cloud computing resource allocation and management such that required service levels are met. Service Level Agreement (SLA) planning and fulfillment 985 provide pre-arrangement for, and procurement of, cloud computing resources for which a future requirement is anticipated in accordance with an SLA.

Workloads layer 990 provides examples of functionality for which the cloud computing environment may be utilized. Examples of workloads and functions which may be provided from this layer include: mapping and navigation 991; software development and lifecycle management 992; virtual classroom education delivery 993; data analytics processing 994; transaction processing 995; and external operations correspondence to container and mutation 996.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for determining command-to-process correspondence, comprising:
   identifying, by a hardware processor, initial processes resulting from executions of container immutability change events for each of multiple initially mutable containers in a cluster, based on an execution time, a process identifier and a process group identifier for each of the container immutability change events;
   checking, by the hardware processor, if an initial process from among the identified initial processes matches an entry in a database that stores external container commands and at least one respective process resulting from executing each of the external container commands; and
   designating, by the hardware processor, a particular external command, from among the external container commands stored in the database, as having a correspondence to the initial process, responsive to the initial process matching the at least one respective process resulting from executing the particular external command.

2. The computer-implemented method of claim 1, further comprising transforming, by the hardware processor based on the correspondence, an initially mutable container into an immutable container with respect to the external container commands.

3. The computer-implemented method of claim 2, wherein said transforming step comprises modifying an existing code of the mutable container to be immutable so as to form the immutable container therefrom.

4. The computer-implemented method of claim 1, further comprising creating the database by executing the external container commands, detecting the at least one respective process resulting from executing each of the external container commands, and mapping each of the external container commands to the at least one respective process resulting therefrom.

5. The computer-implemented method of claim 1, wherein said identifying step comprises determining, for each of the container immutability change events in an order of execution times of the container immutability change events, any of processes as one of the identified initial processes responsive to (i) the process ID of a corresponding one of the container immutability change events being identical to the process group ID of the container immutability change event and (ii) the container immutability change event being a process execution event.

6. The computer-implemented method of claim 1, wherein the container immutability change events are mutation events.

7. The computer-implemented method of claim 1, wherein the computer-implemented method is implemented in a cloud environment.

8. The computer-implemented method of claim 1, further comprising deploying the immutable container in a distributed cloud environment.

9. The computer-implemented method of claim 1, wherein the external container commands comprise an execute command.

10. A computer program product for determining command-to-process correspondence, the computer program product comprising a non-transitory computer readable storage medium having program instructions embodied therewith, the program instructions executable by a computer to cause the computer to perform a method comprising:
   identifying, by a hardware processor of the computer, initial processes resulting from executions of container immutability change events for each of multiple initially mutable containers in a cluster, based on an execution time, a process identifier and a process group identifier for each of the container immutability change events;
   checking, by the hardware processor, if an initial process from among the identified initial processes matches an entry in a database that stores external container commands and at least one respective process resulting from executing each of the external container commands; and
   designating, by the hardware processor, a particular external command, from among the external container commands stored in the database, as having a correspondence to the initial process, responsive to the initial process matching the at least one respective process resulting from executing the particular external command.

11. The computer program product of claim 10, wherein the method further comprises transforming, by the hardware processor based on the correspondence, an initially mutable container into an immutable container with respect to the external container commands.

12. The computer program product of claim 11, wherein said transforming step comprises modifying an existing code of the mutable container to be immutable so as to form the immutable container therefrom.

13. The computer program product of claim 10, wherein the method further comprises creating the database by executing the external container commands, detecting the at least one respective process resulting from executing each of the external container commands, and mapping each of the external container commands to the at least one respective process resulting therefrom.

14. The computer program product of claim 10, wherein said identifying step comprises determining, for each of the container immutability change events in an order of execution times of the container immutability change events, any of processes as one of the identified initial processes responsive to (i) the process ID of a corresponding one of the container immutability change events being identical to the process group ID of the container immutability change event and (ii) the container immutability change event being a process execution event.

15. The computer program product of claim 10, wherein the container immutability change events are mutation events.

16. The computer program product of claim 10, wherein the computer-implemented method is implemented in a cloud environment.

17. The computer program product of claim 10, wherein the method further comprises deploying the immutable container in a distributed cloud environment.

18. The computer program product of claim 10, wherein the external container commands comprise an execute command.

19. A computer processing system for determining command-to-process correspondence, comprising:
   a memory device including program code stored thereon;
   a hardware processor, operatively coupled to the memory device, and configured to run the program code stored on the memory device to
      identify initial processes resulting from executions of container immutability change events for each of multiple initially mutable containers in a cluster, based on an execution time, a process identifier and a process group identifier for each of the container immutability change events;
      check if an initial process from among the identified initial processes matches an entry in a database that stores external container commands and at least one respective process resulting from executing each of the external container commands; and
      designate a particular external command, from among the external container commands stored in the database, as having a correspondence to the initial process, responsive to the initial process matching the at least one respective process resulting from executing the particular external command.

20. The computer processing system of claim 19, wherein said hardware processor is further configured to run the program code to transform, based on the correspondence, an initially mutable container into an immutable container with respect to the external container commands.

21. The computer processing system of claim 20, wherein the hardware processor modifies an existing code of the mutable container to be immutable so as to form the immutable container therefrom.

22. The computer processing system of claim 19, wherein the hardware processor creates the database by executing the external container commands, detecting the at least one respective process resulting from executing each of the external container commands, and mapping each of the external container commands to the at least one respective process resulting therefrom.

23. The computer processing system of claim 19, wherein the processor identified the initial processes by determining, for each of the container immutability change events in an order of execution times of the container immutability change events, any of processes as one of the identified initial processes responsive to (i) the process ID of a corresponding one of the container immutability change events being identical to the process group ID of the container immutability change event and (ii) the container immutability change event being a process execution event.

24. The computer processing system of claim 19, wherein the container immutability change events are mutation events.

25. The computer processing system of claim 19, wherein the computer processing system is implemented as a node in a multi-node cloud environment.

* * * * *